United States Patent [19]

Holland

[11] Patent Number: 5,068,939
[45] Date of Patent: Dec. 3, 1991

[54] BRUSH CONSTRUCTION INCLUDING MOVABLY-MOUNTED BRISTLES

[75] Inventor: Neta Holland, Herzlia, Israel

[73] Assignee: Ohad Paz, Tel-Aviv, Israel

[21] Appl. No.: 457,904

[22] Filed: Dec. 27, 1989

[51] Int. Cl.$^5$ .......................... A46B 13/08; A46B 7/08
[52] U.S. Cl. .......................................... 15/22.1; 15/28; 74/89.12
[58] Field of Search ................... 15/22.1, 22.4, 28, 29, 15/167.1, 201; 74/89.12

[56] References Cited

U.S. PATENT DOCUMENTS

| | | | |
|---|---|---|---|
| 1,557,244 | 10/1925 | Domingue | 15/28 |
| 2,660,745 | 12/1953 | Yusko | 15/22.1 |
| 2,882,544 | 4/1959 | Hadidian | 15/167.1 |
| 3,386,118 | 6/1968 | Morioku et al. | 15/201 |
| 3,683,442 | 8/1972 | Holly | 15/167.1 |
| 4,156,620 | 5/1979 | Clemens | 15/22.1 |
| 4,694,844 | 9/1987 | Berl et al. | 15/167.1 |

Primary Examiner—Edward L. Roberts
Attorney, Agent, or Firm—Benjamin J. Barish

[57] ABSTRACT

A brush includes a plurality of bristle holders each rotatably mounted in the brush head about its own rotary axis, a plurality of crank arms each coupled to one of the bristle holders for oscillating it about its respective rotary axis, and a rod reciprocatably mounted within the handle and carrying a plurality of pins each received in a slot of one of the crank arms to oscillate the respective bristle holder about its rotary axis upon the reciprocation of the rod. In one described embodiment, the reciprocatable rod is connected to a weight slidably mounted in the handle so that the rod is reciprocated by the weight during manual reciprocation of the handle by a user when using the brush. In another described embodiment, the reciprocatable rod is connected to the handle, and the handle is connected to the brush head by a yielding coupling so that the rod is reciprocated by the handle by a user when using the brush.

19 Claims, 4 Drawing Sheets

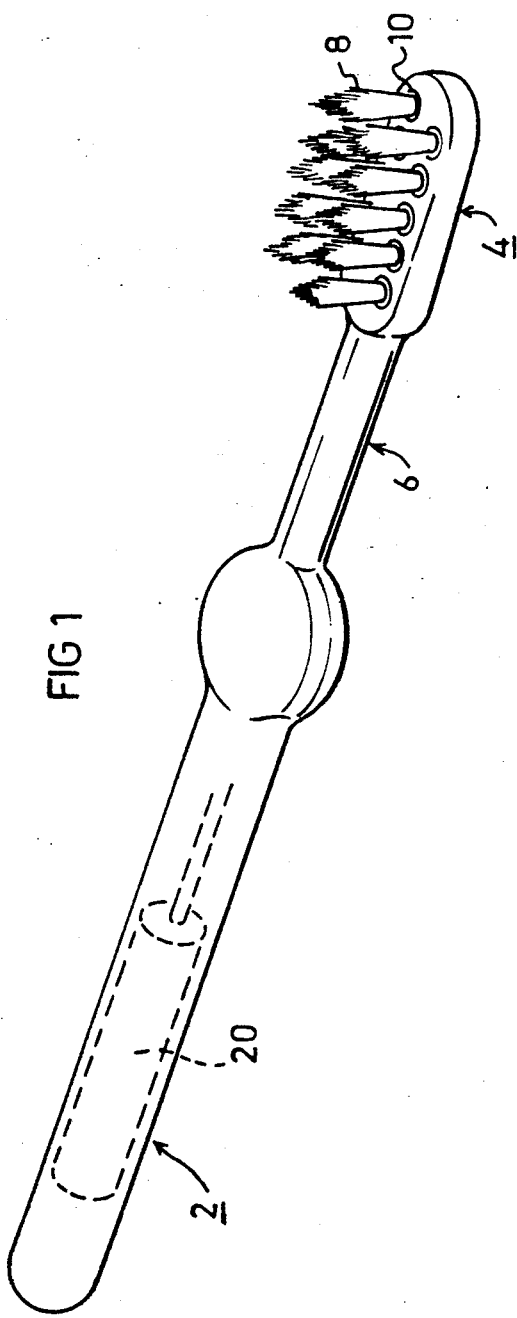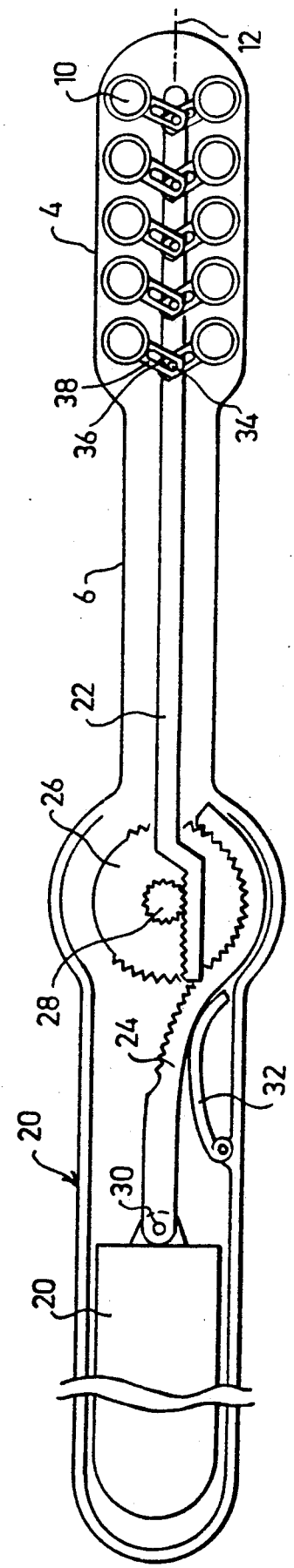

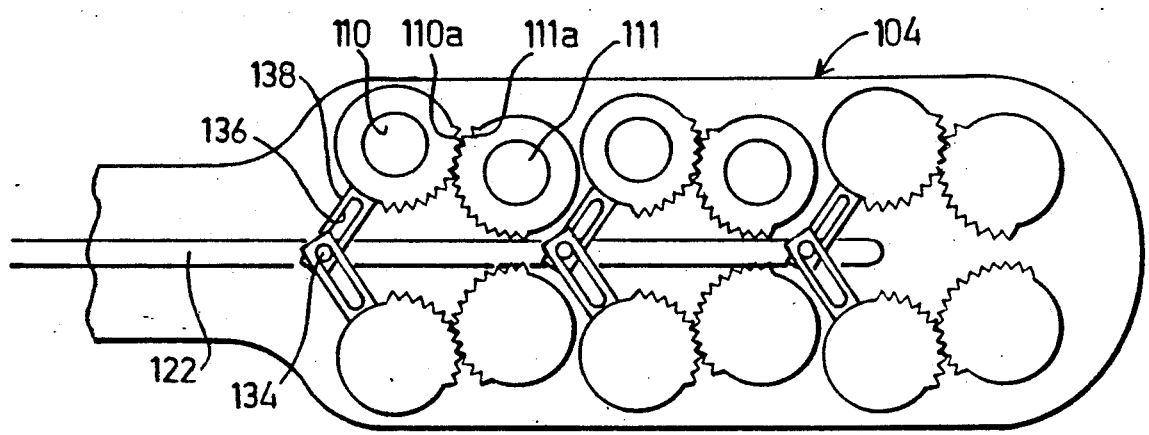
FIG. 5
FIG. 6
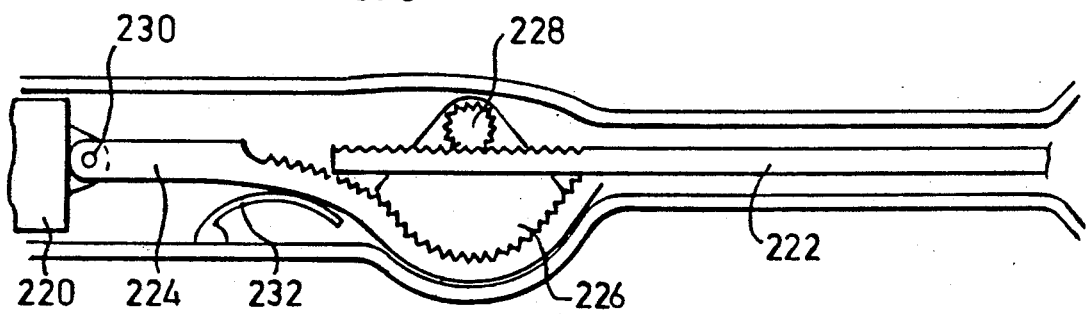
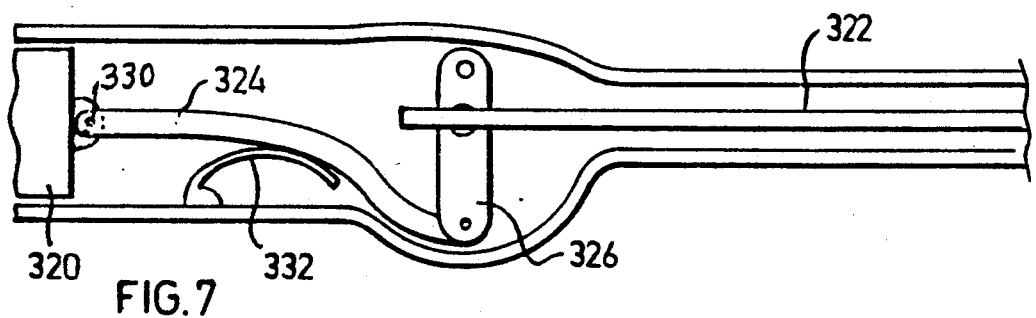
FIG. 7

5,068,939

BRUSH CONSTRUCTION INCLUDING MOVABLY-MOUNTED BRISTLES

BACKGROUND OF THE INVENTION

The present invention relates to a brush construction of the type including a plurality of movably-mounted bristles. The invention is particularly useful in toothbrushes, and is therefore described below with respect to this application.

A large number of toothbrushes having movably-mounted bristles have been developed and are commercially available. These known constructions generally include an electric motor housed within a handle of the toothbrush for rotating or oscillating the bristles; examples of such toothbrushes are described in U.S. Pat. Nos. 3,242,516, 4,156,620, 4,827,550 and 4,845,795. Other toothbrushes are known in which the bristles are rotated by the manual movement of the brush, rather than by an electrical motor; examples of the latter toothbrushes are described in U.S. Pat. Nos. 1,517,320, 3,408,671, 4,010,506, 4,545,087 and 4,763,372.

OBJECTS AND BRIEF SUMMARY OF THE INVENTION

One object of the present invention is to provide a brush of a novel construction for manually oscillating the bristles during use of the brush.

According to the present invention, there is provided a brush, comprising: a handle at one end, and a brush head at the opposite end; a plurality of bristle holders each rotatably mounted in the brush head about its own rotary axis; a plurality of crank arms each coupled to one of the bristle holders for oscillating it about its respective rotary axis; each of the crank arms being formed with an elongated slot; and a reciprocatable member reciprocatably mounted in the handle with respect to the brush head and carrying a plurality of pins each received in the slot of one of the crank arms to oscillate the respective bristle holder about its rotary axis upon the reciprocation of the member.

Several embodiments of the invention are described below for purposes of example.

In one described embodiment, the reciprocatable member is connected to a weight slidably mounted in the handle, and the handle is rigidly connected to the brush head, so that the weight is reciprocated in the handle during manual reciprocation of the handle by a user when using the brush.

In a second described embodiment, the reciprocatable member is fixed to the handle, and the handle is connected to the brush head by a yielding coupling so that the member and handle are reciprocated with respect to the brush head during manual reciprocation of the handle by a user when using the brush.

According to further features in the second described embodiment, the brush head includes a stem telescopingly received by the handle and urged outwardly thereof by a spring interposed between the stem and handle. The yielding coupling further includes an elastic sleeve overlying the juncture of the handle and the stem of the brush head.

According to another aspect of the present invention, there is provided a brush comprising a handle at one end, a brush head at the opposite end, a plurality of bristle holders each mounted for axial and rotary movement about a rotary axis within a socket in the brush head, spring means normally urging the bristle holders outwardly of their respective sockets but permitting inward axial movement of the bristle holders within their respective sockets during use of the brush, and a manually-operated drive for oscillating each bristle holder about its own rotary axis. Such a construction has been found to increase the efficiency of the brushing action, particularly in a toothbrush, since the bristles are thus spring-urged to penetrate into all the spaces of the teeth and between the teeth.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a three-dimensional view illustrating one form of toothbrush constructed in accordance with the present invention;

FIG. 2 is an enlarged view illustrating the internal construction of the toothbrush of FIG. 1;

FIGS. 5-7 illustrate several variations in the construction of the brush of FIGS. 1-4.

DESCRIPTION OF PREFERRED EMBODIMENTS

The Embodiment of FIGS. 1-4

Figure 3:
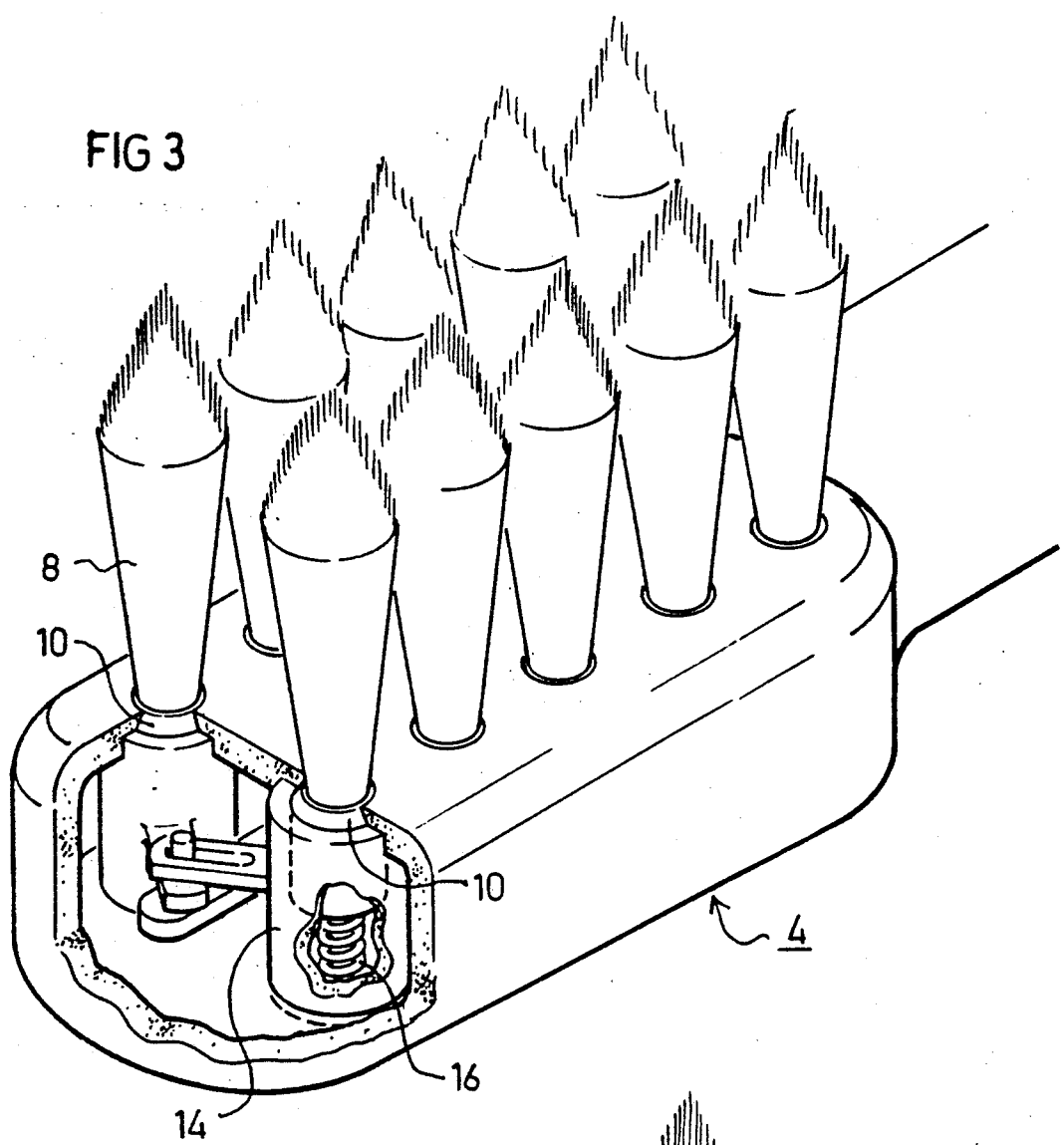
FIG. 3 is a three-dimensional fragmentary view, with parts broken away to show internal structure, more particularly illustrating the construction of the brush head in the brush of FIGS. 1 and 2.

The toothbrush illustrated in FIGS. 1-4 of the drawings comprise a handle 2 at one end, and a brush head 4 at the opposite end connected by a stem 6. The brush head 4 carries a plurality of bristles 8 mounted within bristle holders 10. In the illustrated arrangement, there are ten such bristle holders, arranged in two lines of five each. The two lines are disposed parallel to but on opposite sides of the longitudinal axis 12 (FIG. 2) of the toothbrush.

Figure 4:
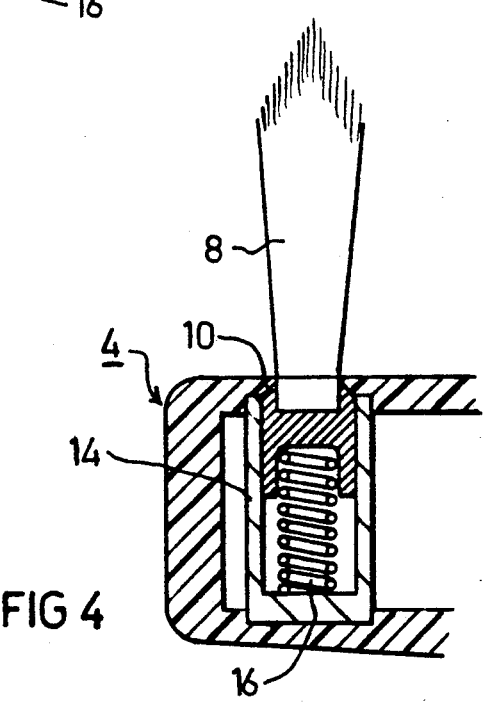
FIG. 4 is an enlarged sectional view illustrating the spring-mounting of each of the bristle holders in the brush of FIGS. 1-3.

As shown particularly in FIGS. 3 and 4, each bristle holder 10 has an external cylindrical configuration and is received within a cylindrical sleeve 14. Each sleeve 14 is in turn received within a cylindrical socket formed in the brush head 4, so as to permit both slidable movement and rotational movement of the bristle holder 10 within its respective cylindrical sleeve 14.

Brush head 4 further includes a spring 16 for each of the bristle holders 10. Each spring 16 is interposed between its respective bristle holder 10 and sleeve 14, and normally urges the bristle holder outwardly of the brush head.

Handle 2 of the illustrated toothbrush further includes a weight 20 which is slidably mounted within handle 2 so as to be reciprocated therein during manual reciprocations of the handle by a user when using the brush. The reciprocations of weight 20 are transmitted, by a transmission within the handle, to the bristle holders 10 to apply rotary movements to the bristle holders during the reciprocations of the weight by the user when using the brush. Each reciprocation of weight 20 rotates each bristle holder 10 for only a fraction, e.g. one-third, of a complete rotation, such that the bristle holders are oscillated about their rotary axes by the reciprocations of the weight.

In the illustrated construction, the transmission coupling weight 20 to the bristle holders 10 includes a reciprocatable member 22 mounted within handle 2 and coupled at one end to weight 20, and at the opposite end to the plurality of bristle holders 10. Member 22 is in the form of a rod having a rack coupled to weight 20 by a second rack 24, a first gear 26, and a second gear 28. Rack 24, having a curved section conforming to the curvature of gear 26, is pivotally mounted to weight 20 by a pin 30 and is urged by a leaf spring 32 into engagement with gear 26 so that the reciprocations of the rack 24 rotate gear 26. Gear 28 is fixed to gear 26 so as to rotate with it. The teeth of gear 28 mesh with the teeth of rack 22 coupled to the bristle holders 10. The latter coupling comprises a plurality of pins 34 formed at the outer end of rack 22 and received within slots 36 formed in crank arms 38 fixed to the bristle holders 10.

Thus, as best seen in FIG. 2, each of the pins 34 at the end of rack 22 is received within the slots 36 of the two crank arms 38 fixed to the pair of bristle holders 10 on opposite sides of the longitudinal axis 12 of the brush head 4.

The operation of the toothbrush illustrated in FIGS. 1-4 of the drawings will be apparent from the above description. Thus, spring 32 continuously urges rack 24 into engagement with gear 26. During use of the toothbrush, the user manually reciprocates the toothbrush parallel to its longitudinal axis 12. This reciprocation of the toothbrush reciprocates weight 20 within handle 2.

During the forward (rightward) strokes of weight 20, rack 24 rotates gears 26 and 28 counterclockwise. Gear 28, meshing with rack 22, therefore moves the rack through a forward stroke, namely in the rightward direction. Pins 34, at the end of rack 22 and received within slots 36 of the crank arms 38, rotate the crank arms fixed to the upper line of bristle holders 10 counter-clockwise, and the crank arms fixed to the lower line of bristle holders clockwise.

During the reciprocations of weight 20 through the return stroke (leftward, FIG. 2), rack 24, gears 26, 28 and rack 22, will move in the opposite direction from their movements during the forward strokes, so as to rotate the bristle holders 10 also in the opposite direction.

It will thus be seen that the manual reciprocations of the toothbrush by the user during the normal brushing action will reciprocate weight 20 and will thereby also oscillate the bristle holders 10 about their respective rotary axes.

It will also be seen that when the bristles 8 are applied to the teeth (or other surfaces being brushed), the spring mounting 16 of the bristle holders 10 will press the bristles against the surface being brushed but will permit the bristles to retract within the respective holders 14 according to the pressure applied. This arrangement enables the bristles to penetrate into all the spaces of the teeth and between the teeth, thereby producing an efficient brushing action.

The Variations of FIGS. 5–8

FIGS. 5–8 illustrate several variations in the construction of the toothbrush.

Thus, as shown in FIG. 5, the bristle holders in the brush head 104 are arranged in pairs 110, 111. Each holder of a pair includes external teeth 110a, 111a, meshing with the external teeth of the other holder of the pair. Thus, the reciprocatory rack 122, which is reciprocated by the weight (not shown), needs to be coupled only to one holder of each pair, e.g., holder 110. The coupled holder is thus oscillated by the rack and in turn oscillates the other holder 111 of the pair via their meshing gear teeth 110a, 111a.

In all other respects, the brush illustrated in FIG. 5 may be constructed as described above, wherein the reciprocatory rack 122 includes a plurality of pins 134 receivable within slots 136 formed in crank arms 138 of one of the holders in each pair.

FIG. 6 illustrates a further variation wherein the reciprocatory rack 222 is coupled to the rack 224 by a sector gear 226 to which is fixed a smaller gear 228 meshing with rack 222. As in the FIGS. 1–4 embodiment, rack 224 is pivotally mounted by pin 230 to the weight 220, and is urged into engagement with sector gear 226 by a leaf spring 232. In all other respects, the brush illustrated in FIG. 7 is constructed and operates in the same manner as described above with respect to FIGS. 1–4.

FIG. 7 illustrates a still further variation, wherein the reciprocatory rack 322 is coupled to the weight 320 by a pair of levers 324, 326. Lever 324 is pivotally mounted at one end to weight 320 by pin 330, and at the opposite end to lever 326 by another pin 332. Lever 326 is in turn pivotally mounted to the brush handle by a further pin 334, and is coupled to the reciprocatory member 322 by a coupling 336 between the two pivotal mountings 332 and 334. In all other respects the brush illustrated in FIG. 7 is constructed and operates in the same manner as described above.

Figure 8:
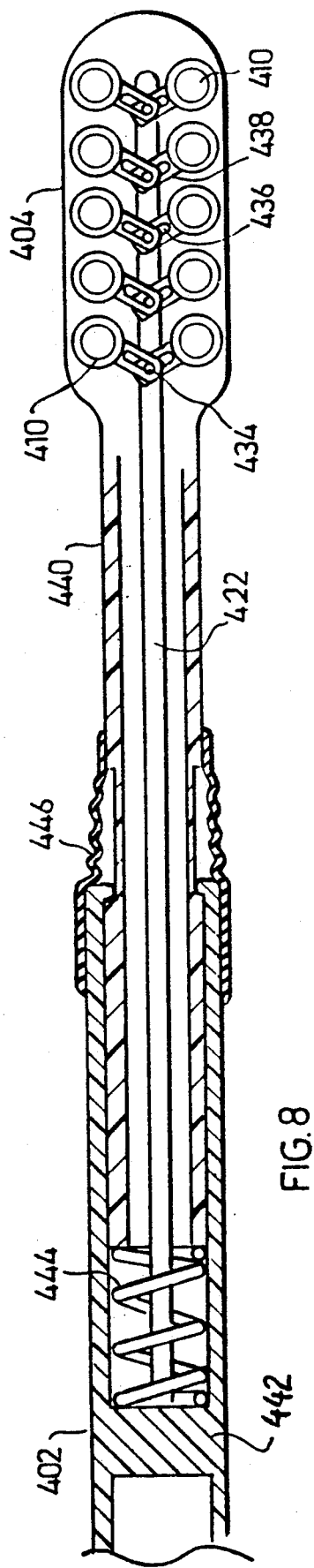
FIG. 8 is a longitudinal sectional view illustrating another toothbrush constructed in accordance with the present invention.

The Embodiment of FIG. 8

FIG. 8 illustrates a further embodiment of the invention, also comprising a handle 402 (the outer end of which is broken away) at one end and a brush head 404 at the opposite end. Brush head 404 is similarly constructed as in the previously-described embodiments, including two lines of bristle holders 410 oscillatably mounted about their individual rotary axes by means of a reciprocatable rod 422. As in the previously-described constructions, reciprocatable rod 422 is formed with five pins 434, each received within the slots 436 of the two crank arms 438 fixed to two bristle holders 410 on the opposite sides of the rod, such that the reciprocation of rod 422 causes all the bristle holders 410 to oscillate about their respective rotary axes.

As distinguished from the previously-described embodiments, however, member 422 is reciprocated with respect to the brush head and bristle holders not by a weight, but rather by the handle 402 itself during the manual reciprocation of the handle by a user when using the toothbrush.

Thus, brush head 404 is not rigidly fixed to handle 402, as in the previously-described embodiments, but rather is yieldingly coupled to the handle. For this purpose, brush head 404 is formed with a hollow stem 440, telescopingly received within handle 402. The end of the reciprocatable rod 422 opposite to that received within the brush head 404 is fixed to a wall 442 within handle 402, and a spring 444 is interposed between the handle wall 442 and the end of stem 440 of the brush head 404. In addition, a resilient sleeve 446, preferably of natural or synthetic rubber, is fixed at one end to handle 402, and at the opposite end to the holow stem 440, so as to cover the juncture between the two, and also to limit the outward movement of the stem 440 with respect to the handle.

In using the toothbrush illustrated in FIG. 8, the user grasps the handle 402 with one hand, applies the bristles (not shown) carried by the bristle holders 410 of the brush head 404 against the user's teeth, and reciprocates the handle. Because of the yielding coupling between the handle 402 and the brush head 404, the handle will tend to move back and forth with respect to the brush head, which will thereby reciprocate rod 422 with respect to the brush head. These reciprocations of rod 422 cause the bristle holders 410, and the bristles carried thereby, to oscillate about their respective rotary axes, thereby increasing the brushing efficiency.

Resilient sleeve 446, which forms the yielding coupling between handle 402 and brush head 404, covers the entry of the brush head stem 440 into the handle, and thereby prevents water from entering the handle.

While the invention has been described with respect to several preferred embodiments, it will be appreciated that many other variations may be made, and that certain features may be used without others. For example, the spring mounting for the bristles could be used in toothbrushes driven by an electric motor, rather than manually as described herein. In addition, still other forms of transmissions may be used for coupling the weight or the handle to the bristle holders. Many other variations, modifications and applications of the invention will be apparent.

What is claimed is:

1. A brush, comprising:
   a handle at one end, and a brush head at the opposite end;
   a plurality of bristle holders each rotatably mounted in the brush head about its own rotary axis;
   a plurality of crank arms each coupled to one of said bristle holders for oscillating it about its respective rotary axis;
   each of said crank arms being formed with an elongated slot;
   and a member mounted in said handle, said member mounted for reciprocable movement with respect to said brush head and carrying a plurality of pins each received in the slot of one of said crank arms to oscillate the respective bristle holder about its rotary axis upon the reciprocation of said member.

2. The brush according to claim 1, wherein said member is connected to a weight slidably mounted in the handle, and the handle is rigidly connected to the brush head, so that the weight is reciprocated in the handle during manual reciprocation of the handle by a user when using the brush.

3. The brush according to claim 1, wherein said member is fixed to the handle, said handle being connected to the brush head by a yielding coupling so that the member and handle are reciprocated with respect to the brush head during manual reciprocation of the handle by a user when using the brush.

4. The brush according to claim 3, wherein said brush head includes a stem telescopingly received by said handle and urged outwardly thereof by a spring interposed between said stem and handle.

5. The brush according to claim 4, wherein said stem is hollow and receives said member therethrough.

6. The brush according to claim 5, wherein said yielding coupling includes a resilient sleeve overlying the juncture of the hollow stem of the brush head and the handle.

7. The brush according to claim 7, wherein said brush head includes a spring for each of said bristle holders normally urging the bristle holder outwardly of the brush head but permitting inward movement of the bristle holder during use of the brush, 8. A brush, comprising:
   a handle at one end, and a brush head at the opposite end connected to the handle by a yielding coupling;
   a plurality of bristle holders each rotatably mounted in the brush head about its own rotary axis;
   a plurality of crank arms each coupled to one of said bristle holders for oscillating it about its respective rotary axis, each of said crank arms being formed with an elongated slot;
   a reciprocatable rod fixed to said handle so as to be reciprocated therewith with respect to said brush head during manual reciprocation of the handle by a user when using the brush, said rod carrying a plurality of pins each received in the slot of one of said crank arms to oscillate the respective bristle holder about its rotary axis upon the reciprocation of said rod.

9. The brush according to claim 8, wherein said yielding coupling includes a stem telescopingly received by said handle and urged outwardly thereof by a spring interposed between said stem and handle.

10. The brush according to claim 9, wherein said stem is hollow and receives said reciprocatable rod therethrough.

11. The brush according to claim 10, wherein said yielding coupling further includes a resilient sleeve overlying the juncture of the hollow stem of the brush head and the handle.

12. A brush, comprising: a handle at one end; a brush head at the opposite end; a plurality of bristle holders each mounted for axial and rotary movement about a rotary axis within a socket in the brush head; spring means normally urging the bristle holders outwardly of their respective sockets but permitting inward axial movement of the bristle holders within their respective sockets during use of the brush; and a manually-operated drive for oscillating each bristle holder about its own rotary axis.

13. The brush according to claim 12, wherein said sockets and bristle holders are of cylindrical configuration, and said spring means comprises a separate spring interposed between the bottom of each bristle holder and its respective socket.

14. The brush according to claim 12, wherein said manually-operated drive for oscillating each bristle holder about its own rotary axis comprises a drive member coupled at one end to said handle and at the opposite end to said bristle holders, and a yielding coupling between said handle and said brush head permitting the handle to be reciprocated with respect to said brush head and thereby to cause the drive member to oscillate the bristle holders.

15. The brush according to claim 14, wherein said manually-operated drive further comprises a plurality of crank arms each coupled to one of said bristle holders for oscillating it about its respective rotary axis, with each of said crank arms being formed with an elongated slot; said drive member carrying a plurality of pins each received in the slot of one of said crank arms to oscillate the respective bristle holder about its rotary axis upon the reciprocation of said drive member.

16. The brush according to claim 14, wherein said yielding-coupling includes a stem telescopingly received by said handle and urged outwardly thereof by a spring interposed between said stem and handle.

17. The brush according to claim 16, wherein said yielding coupling further includes a resilient sleeve overlying the juncture of the hollow stem of the brush head and the handle.

18. The brush according to claim 12, wherein said manually-operated drive member comprises a weight slidably mounted in the handle, the handle being rigidly connected to the brush head, so that the weight is reciprocated in the handle during manual reciprocation of the handle by a user when using the brush; said weight being coupled to said bristle holders so as to oscillate each bristle holder about its own rotary axis when the weight is reciprocated in said handle.

19. The brush according to claim 18, wherein said weight is coupled to said bristle holders by a first rack, a second rack, a first gear, and a second gear; said second rack being pivotally mounted to the weight and spring-urged towards said first gear to rotate it in one direction during the movement of the weight in one direction, and to rotate it in the opposite direction during the movement of the weight in the opposite direction; said second gear being coupled to said first gear and meshing with said first rack to reciprocate it during the rotation of said first and second gears; said first rack being coupled to said bristle holders so as to oscillate each bristle holder about its own rotary axis when the first rack is reciprocated during the movements of said weight in said one and opposite directions.

* * * * *